United States Patent
Kim et al.

(10) Patent No.: US 9,994,849 B2
(45) Date of Patent: Jun. 12, 2018

(54) METHOD OF SEPARATING SENESCENT CELLS USING OVEREXPRESSION OF PROTOCADHERIN

(71) Applicant: Samsung Electronics Co., Ltd., Suwon-si, Gyeonggi-do (KR)

(72) Inventors: Byungju Kim, Suwon-si (KR); Sungjin Ryu, Yongin-si (KR); Sangchul Park, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days. days.

(21) Appl. No.: 15/387,346

(22) Filed: Dec. 21, 2016

(65) Prior Publication Data

US 2017/0183657 A1    Jun. 29, 2017

(30) Foreign Application Priority Data

Dec. 24, 2015  (KR) .......................... 10-2015-0186785

(51) Int. Cl.
*C07H 21/02*    (2006.01)
*C12N 15/113*   (2010.01)
*C12N 5/071*    (2010.01)

(52) U.S. Cl.
CPC .......... *C12N 15/113* (2013.01); *C12N 5/0602* (2013.01); *C12N 2310/14* (2013.01); *C12N 2310/531* (2013.01)

(58) Field of Classification Search
CPC ............................ C12N 15/113; C12N 15/111
See application file for complete search history.

(56) References Cited

U.S. PATENT DOCUMENTS

| | | | |
|---|---|---|---|
| 5,491,069 A | 2/1996 | Dirmi et al. | |
| 7,972,788 B2 | 7/2011 | Miyata et al. | |
| 2002/0192678 A1 | 12/2002 | Chen | |
| 2006/0188983 A1* | 8/2006 | Harris ................. | C12N 5/0607 435/366 |
| 2011/0027796 A1 | 2/2011 | An et al. | |
| 2012/0040855 A1 | 2/2012 | Pan et al. | |
| 2014/0004040 A1* | 1/2014 | Patterson ............... | A61K 38/04 424/1.69 |
| 2014/0255424 A1 | 9/2014 | Wyss-Coray et al. | |
| 2014/0378683 A1* | 12/2014 | Porter .................. | C07D 403/12 544/284 |
| 2016/0161378 A1 | 6/2016 | Kim et al. | |

FOREIGN PATENT DOCUMENTS

| KR | 2009-0098677 A1 | 9/2009 |
|---|---|---|
| KR | 10-1093903 B1 | 12/2011 |
| KR | 10-1318521 B1 | 10/2013 |
| KR | 10-1508129 B1 | 3/2015 |
| KR | 2016-0069427 A | 6/2016 |

* cited by examiner

*Primary Examiner* — Amy H Bowman
(74) *Attorney, Agent, or Firm* — Leydig, Voit & Mayer, Ltd.

(57) ABSTRACT

Provided is a method of separating senescent cells from a sample including the senescent cells, and a method of removing senescent cells from a sample or a subject including the senescent cells.

8 Claims, 8 Drawing Sheets

SEQUENCE LISTING

<160> NUMBER OF SEQ ID NOS: 32

<210> SEQ ID NO 1
<211> LENGTH: 19
<212> TYPE: DNA
<213> ORGANISM: Artificial Sequence
<220> FEATURE:
<223> OTHER INFORMATION: Synthetic Forward primer for PCDH1

<400> SEQUENCE: 1
acgccactcg ggtagtgta                                               19

<210> SEQ ID NO 2
<211> LENGTH: 20
<212> TYPE: DNA
<213> ORGANISM: Artificial Sequence
<220> FEATURE:
<223> OTHER INFORMATION: Synthetic Backward primer for PCDH1

<400> SEQUENCE: 2
tcacggtcga tggaggtctc                                              20

<210> SEQ ID NO 3
<211> LENGTH: 23
<212> TYPE: DNA
<213> ORGANISM: Artificial Sequence
<220> FEATURE:
<223> OTHER INFORMATION: Synthetic Forward primer for PCDH9

<400> SEQUENCE: 3
ctgctctgat tgcctgttta agg                                          23

<210> SEQ ID NO 4
<211> LENGTH: 21
<212> TYPE: DNA
<213> ORGANISM: Artificial Sequence
<220> FEATURE:
<223> OTHER INFORMATION: Synthetic Backward primer for PCDH9

<400> SEQUENCE: 4
accagtctgt agacaaggct g                                            21

<210> SEQ ID NO 5
<211> LENGTH: 19
<212> TYPE: DNA
<213> ORGANISM: Artificial Sequence
<220> FEATURE:
<223> OTHER INFORMATION: Synthetic Forward primer for PCDHA4

<400> SEQUENCE: 5
acctgtccat cgcggaatc                                               19

<210> SEQ ID NO 6
<211> LENGTH: 22
<212> TYPE: DNA
<213> ORGANISM: Artificial Sequence
<220> FEATURE:
<223> OTHER INFORMATION: Synthetic Backward primer for PCDHA4

<400> SEQUENCE: 6
caagaccttt taccagctcg tc                                           22

<210> SEQ ID NO 7
<211> LENGTH: 19
<212> TYPE: DNA
<213> ORGANISM: Artificial Sequence

```
<220> FEATURE:
<223> OTHER INFORMATION: Synthetic Forward primer for PCDHA5

<400> SEQUENCE: 7
atgccagatt cgcggtttc                                              19

<210> SEQ ID NO 8
<211> LENGTH: 23
<212> TYPE: DNA
<213> ORGANISM: Artificial Sequence
<220> FEATURE:
<223> OTHER INFORMATION: Synthetic Backward primer for PCDHA5

<400> SEQUENCE: 8
ctgtacctgt tagttcgggt ttt                                         23

<210> SEQ ID NO 9
<211> LENGTH: 21
<212> TYPE: DNA
<213> ORGANISM: Artificial Sequence
<220> FEATURE:
<223> OTHER INFORMATION: Synthetic Forward primer for PCDHA6

<400> SEQUENCE: 9
ggaaagcaat gtctgctcct c                                           21

<210> SEQ ID NO 10
<211> LENGTH: 20
<212> TYPE: DNA
<213> ORGANISM: Artificial Sequence
<220> FEATURE:
<223> OTHER INFORMATION: Synthetic Backward primer for PCDHA6

<400> SEQUENCE: 10
cctcctcggg tacggagtag                                             20

<210> SEQ ID NO 11
<211> LENGTH: 23
<212> TYPE: DNA
<213> ORGANISM: Artificial Sequence
<220> FEATURE:
<223> OTHER INFORMATION: Synthetic Forward primer for PCDHA12

<400> SEQUENCE: 11
atcggcgtaa actctctttt gac                                         23

<210> SEQ ID NO 12
<211> LENGTH: 22
<212> TYPE: DNA
<213> ORGANISM: Artificial Sequence
<220> FEATURE:
<223> OTHER INFORMATION: Synthetic Backward primer for PCDHA12

<400> SEQUENCE: 12
gctctctgtc caataacttc cg                                          22

<210> SEQ ID NO 13
<211> LENGTH: 21
<212> TYPE: DNA
<213> ORGANISM: Artificial Sequence
<220> FEATURE:
<223> OTHER INFORMATION: Synthetic Forward primer for PCDHB11

<400> SEQUENCE: 13
gagcgggagt tttgtaggca a                                           21
```

<210> SEQ ID NO 14
<211> LENGTH: 19
<212> TYPE: DNA
<213> ORGANISM: Artificial Sequence
<220> FEATURE:
<223> OTHER INFORMATION: Synthetic Backward primer for PCDHB11

<400> SEQUENCE: 14
gtagcacgca aggctcgat                                              19

<210> SEQ ID NO 15
<211> LENGTH: 21
<212> TYPE: DNA
<213> ORGANISM: Artificial Sequence
<220> FEATURE:
<223> OTHER INFORMATION: Synthetic Forward primer for PCDHB13

<400> SEQUENCE: 15
caccctacta acggagagac c                                           21

<210> SEQ ID NO 16
<211> LENGTH: 21
<212> TYPE: DNA
<213> ORGANISM: Artificial Sequence
<220> FEATURE:
<223> OTHER INFORMATION: Synthetic Backward primer for PCDHB13

<400> SEQUENCE: 16
gtcattgaca tcggcgatca g                                           21

<210> SEQ ID NO 17
<211> LENGTH: 21
<212> TYPE: DNA
<213> ORGANISM: Artificial Sequence
<220> FEATURE:
<223> OTHER INFORMATION: Synthetic Forward primer for PCDHGA2

<400> SEQUENCE: 17
cgggcagatt cgctattctg t                                           21

<210> SEQ ID NO 18
<211> LENGTH: 19
<212> TYPE: DNA
<213> ORGANISM: Artificial Sequence
<220> FEATURE:
<223> OTHER INFORMATION: Synthetic Backward primer for PCDHGA2

<400> SEQUENCE: 18
ccggtctatc ctgttcgca                                              19

<210> SEQ ID NO 19
<211> LENGTH: 21
<212> TYPE: DNA
<213> ORGANISM: Artificial Sequence
<220> FEATURE:
<223> OTHER INFORMATION: Synthetic Forward primer for PCDHGA3

<400> SEQUENCE: 19
ttgcctgagt ttccgaaatg g                                           21

<210> SEQ ID NO 20

```
<211> LENGTH: 20
<212> TYPE: DNA
<213> ORGANISM: Artificial Sequence
<220> FEATURE:
<223> OTHER INFORMATION: Synthetic Backward primer for PCDHGA3

<400> SEQUENCE: 20
tcagacaccg agtagcggat                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic Forward primer for PCDHGA7

<400> SEQUENCE: 21
ggcggggact acagaggatt                                              20

<210> SEQ ID NO 22
<211> LENGTH: 22
<212> TYPE: DNA
<213> ORGANISM: Artificial Sequence
<220> FEATURE:
<223> OTHER INFORMATION: Synthetic Backward primer for PCDHGA7

<400> SEQUENCE: 22
cggagtagag aatacgtcct gc                                           22

<210> SEQ ID NO 23
<211> LENGTH: 21
<212> TYPE: DNA
<213> ORGANISM: Artificial Sequence
<220> FEATURE:
<223> OTHER INFORMATION: Synthetic Forward primer for PCDHGA8

<400> SEQUENCE: 23
ttttcctcac ccgatttacc g                                            21

<210> SEQ ID NO 24
<211> LENGTH: 21
<212> TYPE: DNA
<213> ORGANISM: Artificial Sequence
<220> FEATURE:
<223> OTHER INFORMATION: Synthetic Backward primer for PCDHGA8

<400> SEQUENCE: 24
cgctggctgt tacagtaagc a                                            21

<210> SEQ ID NO 25
<211> LENGTH: 19
<212> TYPE: DNA
<213> ORGANISM: Artificial Sequence
<220> FEATURE:
<223> OTHER INFORMATION: Synthetic Forward primer for PCDHGA12

<400> SEQUENCE: 25
caccgggact acaaagggc                                               19

<210> SEQ ID NO 26
<211> LENGTH: 21
<212> TYPE: DNA
<213> ORGANISM: Artificial Sequence
<220> FEATURE:
<223> OTHER INFORMATION: Synthetic Backward primer for PCDHGA12

<400> SEQUENCE: 26
```
atagcgtatc tgggtgcatc c                                          21

<210> SEQ ID NO 27
<211> LENGTH: 19
<212> TYPE: DNA
<213> ORGANISM: Artificial Sequence
<220> FEATURE:
<223> OTHER INFORMATION: Synthetic PCDHA shRNA No. 1

<400> SEQUENCE: 27
cagcagtggc caacagtat                                             19

<210> SEQ ID NO 28
<211> LENGTH: 19
<212> TYPE: DNA
<213> ORGANISM: Artificial Sequence
<220> FEATURE:
<223> OTHER INFORMATION: Synthetic PCDHA shRNA No. 2

<400> SEQUENCE: 28
gagcctacta acagccaaa                                             19

<210> SEQ ID NO 29
<211> LENGTH: 19
<212> TYPE: DNA
<213> ORGANISM: Artificial Sequence
<220> FEATURE:
<223> OTHER INFORMATION: Synthetic PCDHA shRNA No. 3

<400> SEQUENCE: 29
gtaacaagac ccaggagaa                                             19

<210> SEQ ID NO 30
<211> LENGTH: 19
<212> TYPE: DNA
<213> ORGANISM: Artificial Sequence
<220> FEATURE:
<223> OTHER INFORMATION: Synthetic PCDHG shRNA No. 1

<400> SEQUENCE: 30
ctggcaagcg ggatggcaa                                             19

<210> SEQ ID NO 31
<211> LENGTH: 19
<212> TYPE: DNA
<213> ORGANISM: Artificial Sequence
<220> FEATURE:
<223> OTHER INFORMATION: Synthetic PCDHG shRNA No. 2

<400> SEQUENCE: 31
gcaatggcaa caagaagaa                                             19

<210> SEQ ID NO 32
<211> LENGTH: 19
<212> TYPE: DNA
<213> ORGANISM: Artificial Sequence
<220> FEATURE:
<223> OTHER INFORMATION: Synthetic PCDHG shRNA No. 3

<400> SEQUENCE: 32
gcaagaagga gaagaagta                                             19

METHOD OF SEPARATING SENESCENT CELLS USING OVEREXPRESSION OF PROTOCADHERIN

CROSS-REFERENCE TO RELATED APPLICATION

This application claims the benefit of Korean Patent Application No. 10-2015-0186785, filed on Dec. 24, 2015, in the Korean Intellectual Property Office, the entire disclosure of which is hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 7,296 Byte ASCII (Text) file named "726092_ST25.TXT," created on Dec. 21, 2016.

BACKGROUND

1. Field

The present disclosure relates to a method of separating senescent cells using overexpression of protocadherin, and a method of specifically removing senescent cells using the same.

2. Description of the Related Art

Cells cannot continue to divide endlessly, but undergo aging when they reach a certain point. This phenomenon is called replicative cell senescence. However, not all cells undergo a synchronized aging pattern, and therefore, cells cultured in a mammalian tissue or a culture dish are heterogeneous according to senescence level of senescent cells (Heterogeneity of senescence).

Senescent cells are characterized in that they show a flat and enlarged morphology with increased beta-galactosidase (β-galactosidase) activity at a particular pH. Senescent cells can be selectively distinguished by these features, but it is difficult to separate senescent cells.

Accordingly, there is a demand for a method of selectively separating fully senescent cells to be used in subsequent experiments. This invention provides such a method

SUMMARY

An aspect of the invention provides a method of separating senescent cells from a sample including the senescent cells.

Another aspect of the invention provides a method of removing senescent cells from a sample or a subject including the senescent cells.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1A:
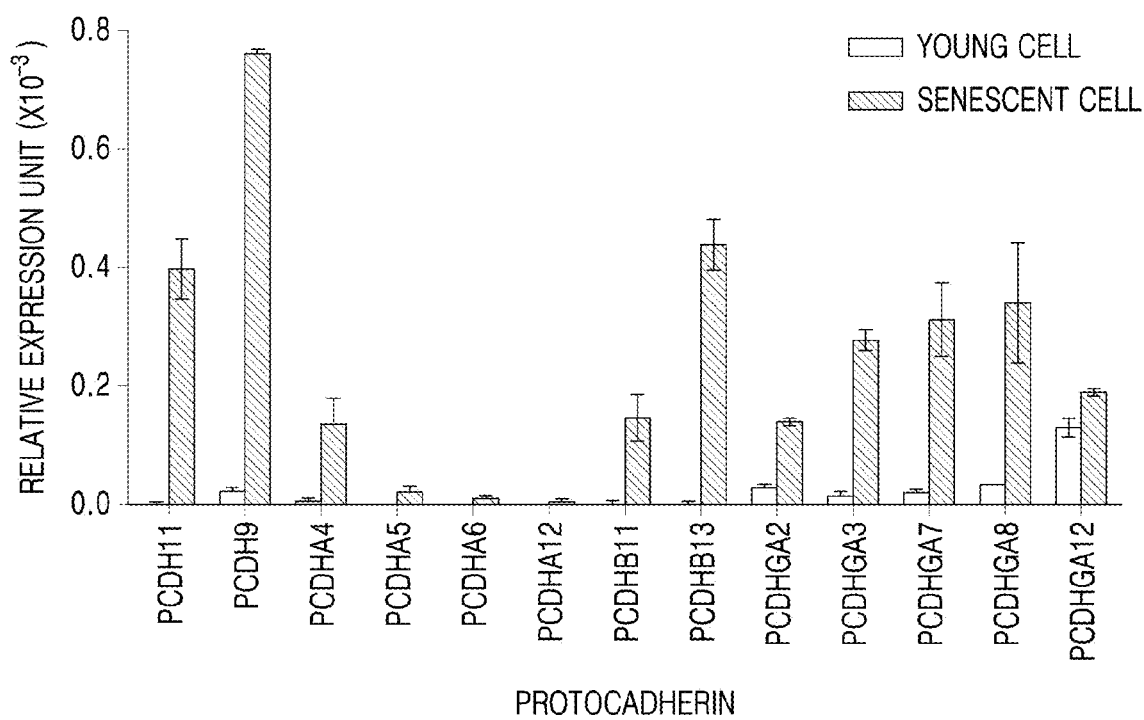
FIG. 1A is a graph showing the results of qPCR studies determining the mRNA expression level of various protocadherins in senescent cells and young cells.

An aspect of the invention provides a method of separating senescent cells from a sample including the senescent cells, the method including contacting the sample including the senescent cells with a non-pretreated vessel to attach the senescent cells to the vessel; and separating the adherent senescent cells from the vessel. As cultured cells do not adhere to and grow on untreated plastic and glass vessels, cell culture is conventionally performed in plastic or glass containers that have been treated to allow cells to adhere to the surface of the container and facilitate propagation. Plastic vessels, for instance, are typically treated to change the hydrophobic plastic surface to a hydrophilic surface. Glass and plastic vessels also can be treated with a variety of biological matrices to allow for cell growth. Without wishing to be bound by any particular theory or mechanism, it is believed that senescent cells are different and, unlike non-senescent cells, can grow on non-pretreated plastic and glass surfaces. In this way, the method allows for senescent cells to be separated from non-senescent cells.

Senescence refers to an array of changes that occurs over time. Senescence in a cell or subject is indicated by changes in the cell or subject that may include, as compared with a reference cell or a reference subject, reduction in proliferation of a cell, accumulation of lipofuscin, increase in β-galactosidase activity, increase in mitochondrial reactive oxygen species, or a combination thereof. The reference cell may be a cell showing a doubling time (DT)≤1 day. The reference subject may be a subject containing at least a cell showing a doubling time (DT)≤1 day. The accumulation of lipofuscin may be determined by micrograph as lipofuscin is granular yellow-brown pigment granules. The mitochondrial reactive oxygen species may be detected by any method known in the art, for example, fluorescent probes and immunoassays. When compared to a reference cell, a senescent cell may show a higher expression level of messenger RNA (mRNA) of protocadherin or a protocadherin protein than a young cell, a higher DNA methylation level in a protocadherin gene cluster than a young cell, β-galactosidase activity, a flat morphology, or a combination thereof. A young cell, as defined herein, as compared with the reference cell, may be cells with increased proliferation, decreased accumulation of lipofuscin, increased β-galactosidase activity, or a combination thereof. For example, a cell showing a DT≤1 day may be referred to as a young cell. A cell showing a DT≥14 days may be referred to as a senescent cell. For example, a cell having a doubling time that is twice or more, three times or more, four times or more, five times or more, six times or more, seven times or more, nine times or more, ten times or more, fourteen times or more, or twenty times or more than that of a cell passaged twice may be defined as a senescent cell. In the case of a human, a cell that is taken from a person about 30 years old or older, about 40 years old or older, about 50 years old or older, about 60 years old or older, about 70 years old or older, about 80 years old or older, about 90 years old or older, or about 100 years old or older may be defined as a senescent cell.

Protocadherin gene is located on chromosome 5 and forms a gene clustering in human. A total of 52 human genes belongs to this cluster, and is largely divided into 3 families including the alpha family containing 15 genes, the beta family containing 16 genes, and the gamma family containing 21 genes. Among them, the gamma family is further divided into a type and b type. Protocadherin mainly plays a role in cell adhesion and cell-cell connection.

The sample may include a heterogeneous group of cells varying in a senescence level. Not all cells undergo a synchronized aging pattern, and therefore, cells in a mammalian tissue or cultured in a culture dish may be heterogeneous with respect to senescence. The sample may include a population of cells of which, for example, about 1% to about 50%, about 5% to 40%, or about 10% to 30% are senescent cells.

The sample may contain any type of cells. The cells may include, for example, a nerve cell, an immune cell, an epithelium cell, a germ cell, muscle cell, or a cancer cell. The cells may include a fibroblast or an early senescent cell. The early senescent cell may be a cell derived from a patient with progeria.

The non-pretreated vessel may be a vessel without pretreatment for cell culture. Examples of pretreatment for cell culture include coating with gelatin, collagen, fibronectin, polylysine, vitronectin, osteopontin, hydrogel, laminin, a fragment thereof, or a mimetic thereof; modification of the surface of the vessel with a compound having a hydroxy group or a carboxyl group; coating with Matrigel; coating with an extracellular matrix or a fragment thereof; treatment to convert a hydrophobic plastic (e.g., polystyrene) surface to a hydrophilic surface; or a combination thereof.

The vessel may be made of plastic (e.g., polystyrene) or glass, or a combination thereof. The vessel may be, for example, a Petri dish. In one embodiment, the plastic or polystyrene vessel without pre-treatment comprises a hydrophobic surface.

The contacting (e.g., culturing) of the sample in the vessel may be performed for about 30 minutes to about 24 hours. The contacting may be performed for about 30 minutes to about 18 hours, about 1 hour to about 12 hours, about 2 hours to about 8 hours, about 2 hours to about 6 hours, or about 2 hours to about 4 hours. For example, the sample including the senescent cells may be seeded in the vessel to contact the sample with the vessel. The contacting may be performed at room temperature or about 37° C. By contacting with the non-pretreated vessel, a significant proportion of the senescent cells adheres to the vessel and proliferates in the vessel. In contrast, young cells will not adhere to the vessel in significant proportion, or the young cells may not proliferate, even though they adhere to the vessel.

The separating the senescent cells from the vessel may comprise applying trypsin, collagenase, hyaluronidase, DNase, elastase, papain, protease type XIV, or a combination thereof to the senescent cells adhered to the vessel. The separated senescent cells may have characteristics of senescent cells. For example, the separated senescent cells may show a higher expression level of mRNA of protocadherin or a protocadherin protein than young cells, a higher DNA methylation level in a protocadherin gene cluster than young cells, 3-galactosidase activity, or a flat morphology. The separated senescent cells may include, for example, senescent cells of more than about 50% to 100%, about 70% to 100%, or about 90% to 100%.

The method may further include culturing the separated senescent cells in a cell culture vessel. The cell culture vessel may be pre-treated for cell culture. The pretreatment for cell culture may be the same as described above.

Another aspect of the invention provides a method of removing senescent cells from a sample or from a subject including the senescent cells, the method including administering an agent inhibiting expression or function of protocadherin to the sample or the subject including the senescent cells.

The senescence, senescent cells, sample, and protocadherin are the same as described above.

The term "expression" refers to a process whereby information from a gene is used to synthesize a gene product. The gene product may be RNA, a polypeptide, or a protein. The expression of protocadherin may be a process whereby RNA, a polypeptide, or a protein of protocadherin is synthesized from a protocadherin gene.

The agent inhibiting expression or function of protocadherin refers to an agent decreasing expression of protocadherin to decrease the amount of RNA, polypeptide, or protein of protocadherin, or an agent inhibiting activity of protocadherin. The agent may be selected from the group consisting of small hairpin RNA (shRNA), short interfering RNA (siRNA), microRNA (miRNA), ribozyme, antisense oligonucleotide, an antibody or an antigen-binding fragment thereof, and aptamer. The shRNA may be an RNA molecule having a hairpin structure capable of silencing expression of a target gene via RNA interference. The siRNA is an RNA molecule involved in RNA interference, and inhibits gene expression by suppressing production of a particular protein. The shRNA or siRNA may have a length of 10 nucleotides (hereinafter, referred to as 'nt') to 50 nt, 15 nt to 40 nt, 20 nt to 30 nt, or 21 nt to 23 nt. The shRNA or siRNA may be commercially available. miRNA is a small RNA that functions to control gene expression of an organism and has a length of about 17 nt to about 25 nt. miRNA functions to increase or decrease production of a particular protein by complementary binding with mRNA. Ribozyme is RNA that functions as an enzyme, and refers to RNA that functions as an enzyme catalyzing biochemical reactions such as RNA splicing, tRNA synthesis, protein synthesis, etc. Antisense oligonucleotide is a single-stranded DNA or RNA complementary to a particular sequence, and functions to increase or decrease production of a particular protein by complementary binding with mRNA. The antibody or the antigen-binding fragment thereof may bind to protocadherin to inhibit activity of protocadherin. The antibody may be a whole antibody. The antigen-binding fragment may be a single-domain antibody, Fab, Fab', or a single-chain variable fragment (scFv).

The subject may be a mammal, for example, human, cow, horse, pig, dog, sheep, goat, rat, mouse, rabbit, or cat.

The subject may be a subject having an aging-related symptom or disease, or a subject at risk of having an aging-related symptom or disease. The aging-related symptom or disease may be skin wrinkle, slow scar regeneration, a degenerative brain disease, stroke, diabetes, arthritis, artery hardening, a heart disease, alopecia, osteoporosis, sarcopenia, progeria, lysosome storage disease, or a combination thereof.

Administering the agent to a sample may comprise applying the agent inhibiting expression or function of protocadherin to the sample. Cell adhesion by protocadherin may be specific to senescent cells. By applying the agent inhibiting expression or function of protocadherin to the sample, senescent cells may be detached from the vessel over time, and eventually die, to be selectively removed from the sample.

The administering to a subject may be performed, for example, in the range of about 0.001 mg/kg to about 100 mg/kg, about 0.01 mg/kg to about 10 mg/kg, or about 0.1 mg/kg to about 1 mg/kg per adult once a day, several times a day, once a few days during a period of one day to 1 year. The administration may be performed by a method known in the art. The administration may be performed directly to a subject by any means, for example, oral, intravenous, intramuscular, oral, transdermal, mucosal, intranasal, intratracheal, or subcutaneous administration. The administration may be topical or systemic administration. The administration may be topical administration to a tissue including senescent cells.

When the agent inhibiting expression or function of protocadherin is administered to the subject, an aging-related symptom or disease may be prevented or treated by the administration. The term "prevention" means all of the actions by which the occurrence of aging-related symptom or disease is restrained or retarded by administration of the composition. The term "treatment" means all of the actions by which the symptoms of aging-related symptom or disease have taken a turn for the better or been modified favorably by administration of the composition.

According to the method of separating senescent cells from a sample including the senescent cells, and the method of removing senescent cells from a sample or a subject including the senescent cells, the senescent cells may be specifically separated from the sample and the separated senescent cells may be used to perform subsequent experiments. Further, the senescent cells may be specifically removed from the sample or the subject to efficiently prevent or treat an aging-related symptom or disease.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items.

Hereinafter, the present invention will be described in more detail with reference to Examples. However, these Examples are for illustrative purposes only, and the scope of the invention is not intended to be limited by these Examples.

Example 1. Separation or Removal of Senescent Cells Using Overexpression of Protocadherin 1. Examination of Expression of Protocadherin Gene Cluster in Senescent Cells (1) Examination of Protocadherin mRNA and Protein Levels in Senescent Cells First, human dermal fibroblast (HDF) M11 cells obtained from neonatal foreskin were cultured in a DMEM medium containing high concentration of glucose, glutamine, and pyruvate and medium supplemented with 10% (v/v) FBS and 1× penicillin/streptomycin under conditions of 37° C. and 5% $CO_2$ to obtain young cells (i.e., cells that were passaged 10 times or less and whose doubling time was about 1 day). The prepared young cells were seeded in a 6-well plate at a density of about 20,000 cells/well, and continuously cultured under conditions of 37° C. and 5% $CO_2$ to prepare senescent cells (number of passage: 52) having a doubling time of about 14 days. mRNA and protein were obtained from the prepared cells.

mRNAs obtained from the young cells and senescent cells were subjected to quantitative polymerase chain reaction (qPCR) using the following primer sets.

```
PCDH1 forward primer:
                                    (SEQ ID NO: 1)
5'-ACGCCACTCGGGTAGTGTA-3'

PCDH1 reverse primer:
                                    (SEQ ID NO: 2)
5'-TCACGGTCGATGGAGGTCTC-3'

PCDH9 forward primer:
                                    (SEQ ID NO: 3)
5'-CTGCTCTGATTGCCTGTTTAAGG-3'

PCDH9 reverse primer:
                                    (SEQ ID NO: 4)
5'-ACCAGTCTGTAGACAAGGCTG-3'

PCDHA4 forward primer:
                                    (SEQ ID NO: 5)
5'-ACCTGTCCATCGCGGAATC-3'

PCDHA4 reverse primer:
                                    (SEQ ID NO: 6)
5'-CAAGACCTTTTACCAGCTCGTC-3'

PCDHA5 forward primer:
                                    (SEQ ID NO: 7)
5'-ATGCCAGATTCGCGGTTTC-3'

PCDHA5 reverse primer:
                                    (SEQ ID NO: 8)
5'-CTGTACCTGTTAGTTCGGGTTTT-3'

PCDHA6 forward primer:
                                    (SEQ ID NO: 9)
5'-GGAAAGCAATGTCTGCTCCTC-3'

PCDHA6 reverse primer:
                                    (SEQ ID NO: 10)
5'-CCTCCTCGGGTACGGAGTAG-3'

PCDHA12 forward primer:
                                    (SEQ ID NO: 11)
5'-ATCGGCGTAAACTCTCTTTTGAC-3'

PCDHA12 reverse primer:
                                    (SEQ ID NO: 12)
5'-GCTCTCTGTCCAATAACTTCCG-3'

PCDHB11 forward primer:
                                    (SEQ ID NO: 13)
5'-GAGCGGGAGTTTTGTAGGCAA-3'

PCDHB11 reverse primer:
                                    (SEQ ID NO: 14)
5'-GTAGCACGCAAGGCTCGAT-3'

PCDHB13 forward primer:
                                    (SEQ ID NO: 15)
5'-CACCCTACTAACGGAGAGACC-3'

PCDHB13 reverse primer:
                                    (SEQ ID NO: 16)
5'-GTCATTGACATCGGCGATCAG-3'
```

-continued

PCDHGA2 forward primer:
(SEQ ID NO: 17)
5'-CGGGCAGATTCGCTATTCTGT-3'

PCDHGA2 reverse primer:
(SEQ ID NO: 18)
5'-CCGGTCTATCCTGTTCGCA-3'

PCDHGA3 forward primer:
(SEQ ID NO: 19)
5'-TTGCCTGAGTTTCCGAAATGG-3'

PCDHGA3 reverse primer:
(SEQ ID NO: 20)
5'-TCAGACACCGAGTAGCGGAT-3'

PCDHGA7 forward primer:
(SEQ ID NO: 21)
5'-GGCGGGGACTACAGAGGATT-3'

PCDHGA7 reverse primer:
(SEQ ID NO: 22)
5'-CGGAGTAGAGAATACGTCCTGC-3'

PCDHGA8 forward primer:
(SEQ ID NO: 23)
5'-TTTTCCTCACCCGATTTACCG-3'

PCDHGA8 reverse primer:
(SEQ ID NO: 24)
5'-CGCTGGCTGTTACAGTAAGCA-3'

PCDHGA12 forward primer:
(SEQ ID NO: 25)
5'-CACCGGGACTACAAAGGGC-3'

PCDHGA12 reverse primer:
(SEQ ID NO: 26)
5'-ATAGCGTATCTGGGTGCATCC-3'

The result of qPCR is shown in FIG. 1A. PCDHA4, PCDHA5, PCDHA6, and PCDHA12 belong to protocadherin alpha family, PCDHB11 and PCDHB13 belong to protocadherin beta family, and PCDHGA2, PCDHGA3, PCDHGA7, PCDHGA8, and PCDHGA12 belong to protocadherin gamma family.

Figure 1B:
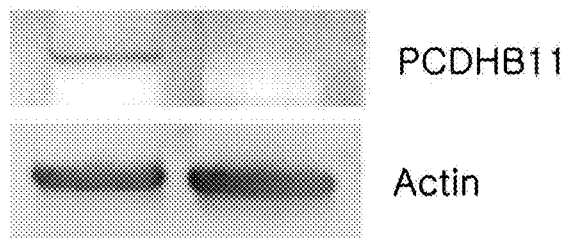
FIG. 1B is a graph showing the result of immunoblotting studies determining the level of protocadherin using an anti-protocadherin antibody in senescent cells and young cells.

The proteins obtained from the young and senescent cells were subjected to immunoblotting using an anti-protocadherin antibody (Santa Cruz, sc-109760), and the result is shown in FIG. 1B.

As shown in FIGS. 1A and 1B, it was confirmed that expression of protocadherin clusters of protocadherin alpha, beta, and gamma families were significantly increased in the senescent cells, compared to the young cells. Since a major function of protocadherin is cell adhesion, the senescent cells were found to have stronger cell adhesion than the young cells.

(2) Examination of DNA Methylation

DNA methylation is an epigenetic marker, and thus changes thereof are expected during the aging process of human. DNA methylation of protocadherin gene was examined in young cells and senescent cells.

Genomic DNAs were isolated from the young cells and the senescent cells prepared in 1.(1). DNA methylation levels of protocadherin gene clusters in the isolated genomic DNAs were detected using a DNA methylation array (Illumina). The detected DNA methylation levels were aligned using UCSC genome bioinformatics browser.

DNA methylation levels of protocadherin genes were increased in senescent cells, compared to the young cells. Therefore, it was confirmed that increased expression level of protocadherin is accompanied by increased DNA methylation level of protocadherin gene.

2. Examination of Adhesion of Senescent Cells

Based on the fact that senescent cells show increased expression of protocadherin, compared to young cells, as described in 1.(1), it was examined whether senescent cells have specific and strong adhesion, compared to young cells.

When senescent cells were cultured in a culture dish, the degree of senescence was determined by doubling time (DT), but actually, cells varying in the degree of senescence coexist. To examine whether senescent cells have strong adhesion, compared to young cells, each about 10,000 of senescent cells and young cells were seeded in a plastic dish (Petri dish, SPL Life Sciences). In detail, cells of passage 7 (DT about 1 day), passage 34 (DT about 3 day), passage 47 (DT about 10 day), and passage 50 (DT about 14 day) were seeded, and the used plastic dish was a plain plastic dish without pretreatment for cell adhesion.

The seeded cells were cultured under conditions of 37° C. and 5% $CO_2$ for about 2 hours, about 4 hours, about 6 hours, and about 8 hours. To remove non-adherent cells, the plastic dish was washed with PBS twice, and the adherent cells on the plastic dish were observed and counted under a microscope. Further, crystal violet (Sigma, HT90132) was applied to the adherent cells for cell staining.

Figure 2A:
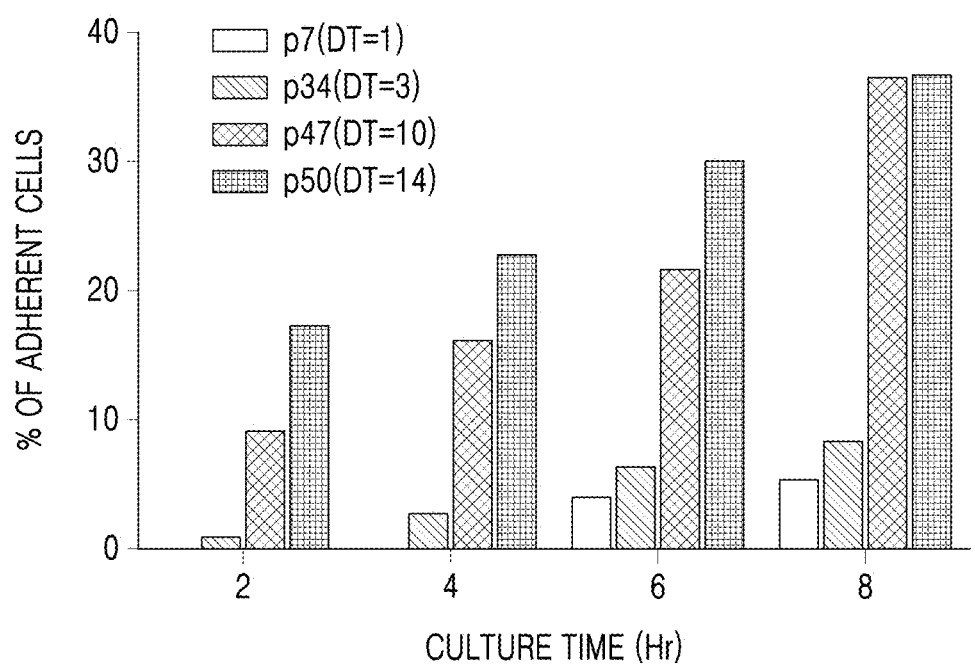
FIG. 2A is a graph showing a percentage of adherent cells on a plastic dish (p=number of passage, DT=doubling time)
Figure 2B:
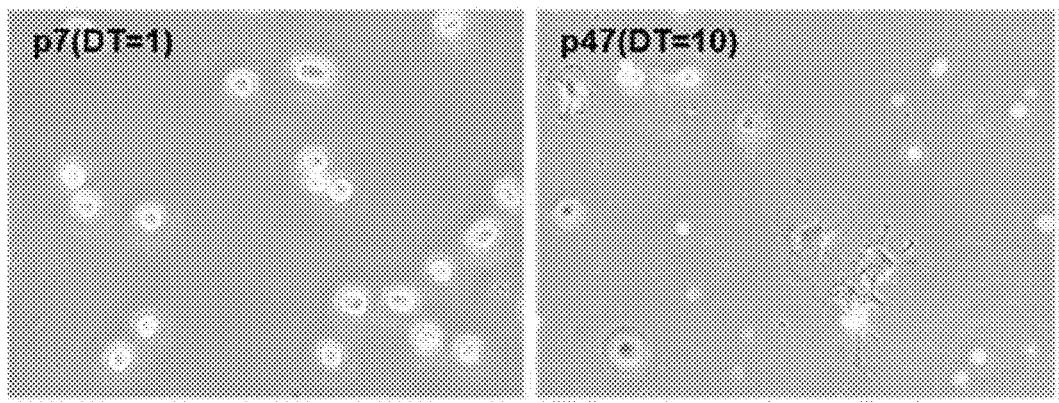
FIGS. 2B and 2C are a microscopic image and a crystal violet staining image of adherent cells on a plastic dish, respectively.
Figure 2C:
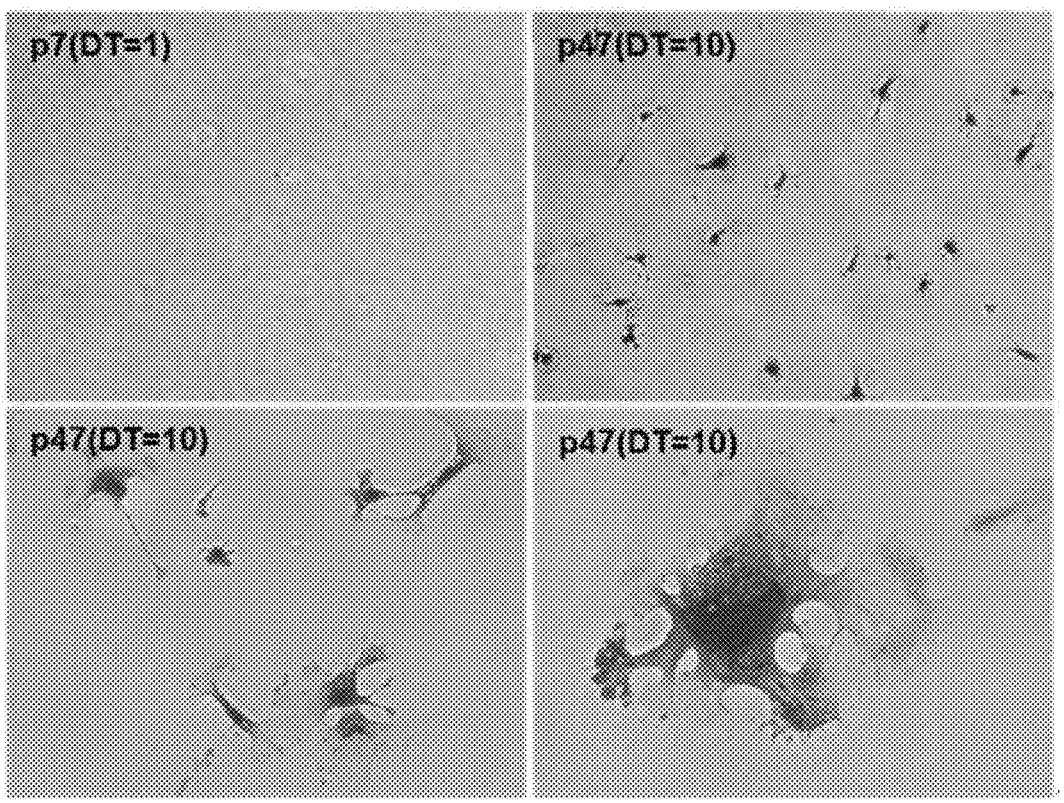

A percentage of the adherent cells on the plastic dish is shown in FIG. 2A, and an image of the cells and an image of the crystal violet-stained cells are shown in FIGS. 2B and 2C, respectively.

As shown in FIGS. 2A through 2C, it was observed that young cells hardly adhered to the plastic dish at an initial time, or a small number of cells adhered to the plastic dish even though they were cultured for a long time, and the morphology was not as healthy as the original young cells. In contrast, it was observed that a larger number of senescent cells adhered to the plastic dish with aging. It was also observed that senescent cells strongly adhered to the plastic dish while growing, compared to young cells.

Cells are generally cultured in a culture dish pretreated for cell culture because of their weak adhesion to a non-treated dish. However, senescent cells show strong adhesion, and therefore, they grow well in a non-pretreated plastic dish. Accordingly, it was confirmed that senescent cells may be specifically separated from cells varying in the degree of senescence by culturing the cells in a non-pretreated plastic dish.

3. Examination Whether Senescent Cells Cultured in Plastic Dish Grow in Cell Culture Dish Trypsin (ThermoFisher Scientific, R-001-100) was applied to the senescent cells cultured in a plastic dish for about 6 hours in 2. to separate cells. All of the separated cells were seeded in a cell culture dish (Falcon Tissue Culture Dish), and cultured under conditions of 37° C. and 5% $CO_2$ for about 12 hours. It was confirmed that the cultured cells grew well, like general senescent cells.

Therefore, it was confirmed that the senescent cells separated using a plastic dish may be further cultured and maintained.

4. Examination Whether Senescent Cells Cultured in Plastic Dish Retain Senescence Property Beta-galactosidase activity was measured as a senescence marker. As described in 2., cells at varying numbers of passage were attached to a plastic dish, respectively. Non-adherent floating cells and adherent cells were obtained separately. Respective proteins were obtained from the floating cells and the adherent cells.

Figure 3A:
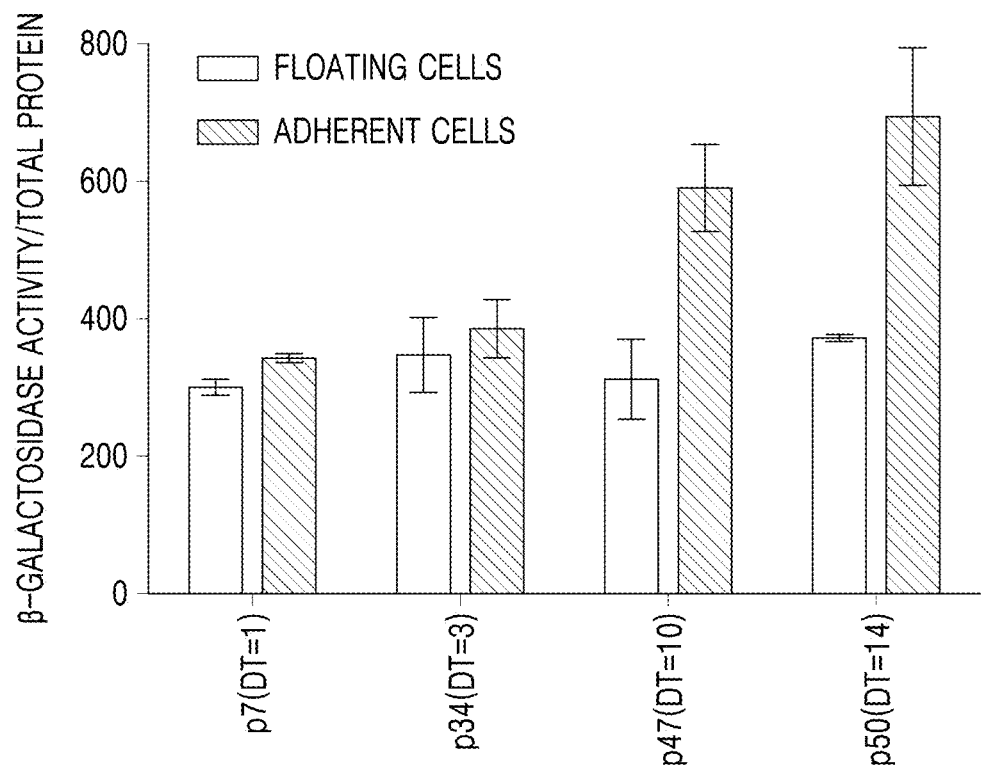
FIG. 3A is a graph showing beta-galactosidase activity of proteins obtained from adherent cells on a plastic dish or non-adherent floating cells.

Beta-galactosidase activities of the obtained proteins were measured using a β-galactosidase enzyme analysis system (Promega, E2000), and the result is shown in FIG. 3A. As shown in FIG. 3A, the adherent cells on the plastic dish showed higher beta-galactosidase activity than the floating cells, indicating that although cells have a doubling time of about 14 days, cells varying in the degree of senescence actually coexist.

Figure 3B:
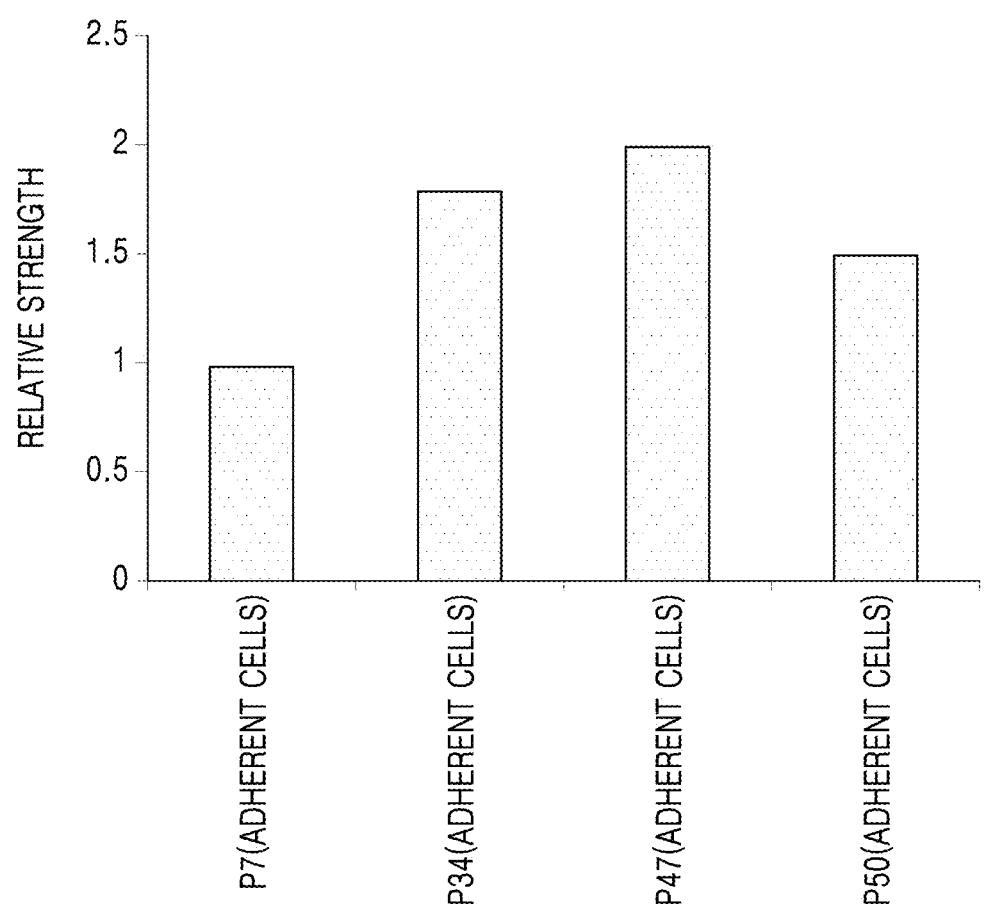
FIG. 3B is a graph showing the result of immunoblotting the proteins of the adherent cells using an anti-PCDHGA2 antibody.

Further, the proteins of the floating cells and adherent cells were subjected to immunoblotting using an anti-PCD-HGA2 antibody (Santa Cruz, sc-81818) and an anti-actin antibody (Sigma, A2228). No significant detection of protocadherin was observed in the floating cells. Strength of protocadherin of the adherent cells was measured using a densitometer, and the result is shown in FIG. 3B. As shown in FIG. 3B, the amount of protocadherin was increased in the adherent cells.

Therefore, it was confirmed that the adherent cells on the plastic dish retain beta-galactosidase activity as a senescence property and show high protocadherin expression.

5. Removal of Senescent Cells Using Protocadherin shRNA

In order to examine whether suppression of protocadherin expression in senescent cells affects cell adhesion, small hairpin RNAs (shRNAs) targeting protocadherin alpha, beta 11, and gamma families were injected into senescent cells and their effects were examined.

Young cells and senescent cells were prepared as described in 1., and about 10,000 cells were seeded on a cell culture dish (Falcon Tissue Culture Dish).

shRNAs targeting protocadherin alpha, beta 11, and gamma families were applied to the seeded cells. Three kinds of shRNAs (Dharmacon) of the following nucleotide sequences, which target protocadherin alpha, were mixed and used:

```
PCDHA shRNA NO. 1:
                            (SEQ ID NO: 27)
5'-CAGCAGTGGCCAACAGTAT-3'

PCDHA shRNA NO. 2:
                            (SEQ ID NO: 28)
5'-GAGCCTACTAACAGCCAAA-3'

PCDHA shRNA NO. 3:
                            (SEQ ID NO: 29)
5'-GTAACAAGACCCAGGAGAA-3'
```

Further, PCDHB11 shRNA (Dharmacon, Cat. No. RHS4533-EG56125), which targets protocadherin beta 11, was mixed and used.

Furthermore, three kinds of shRNAs (Dharmacon) of the following nucleotide sequences, which target protocadherin gamma, were mixed and used:

```
PCDHG shRNA NO. 1:
                            (SEQ ID NO: 30)
5'-CTGGCAAGCGGGATGGCAA-3'

PCDHG shRNA NO. 2:
                            (SEQ ID NO: 31)
5'-GCAATGGCAACAAGAAGAA-3'

PCDHG shRNA NO. 3:
                            (SEQ ID NO: 32)
5'-GCAAGAAGGAGAAGAAGTA-3'
```

Figure 4A:
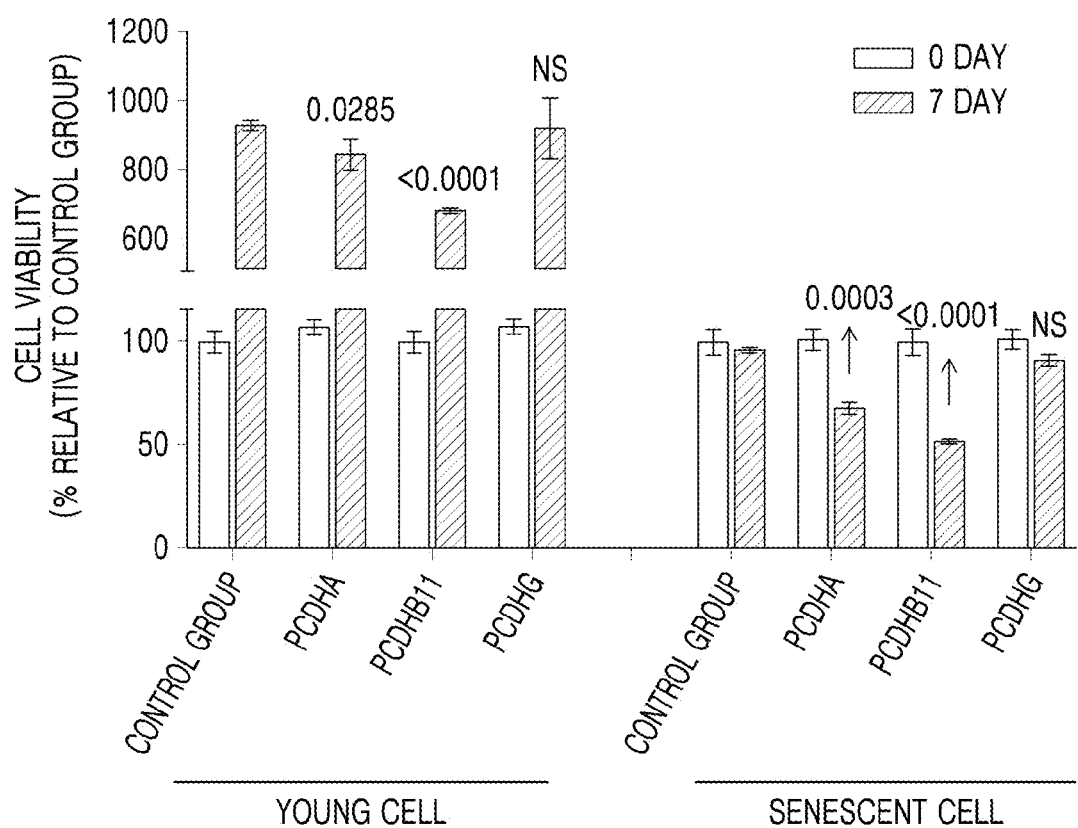
FIG. 4A is a graph showing cell viability (%) of adherent cells on a culture dish upon application of PCDHA shRNAs to senescent cells and young cells.

A cell culture medium containing the siRNAs were exchanged once about three days, and cultured for about 7 days under conditions of 37° C. and 5% $CO_2$. The number of adherent cells on the culture dish was counted under a microscope, and cell viability (%) is shown in FIG. 4A. As a negative control, non-shRNA treated cells were used.

As shown in FIG. 4A, PCDHA shRNA-treated senescent cells were detached from the cell culture dish over time, and eventually died. In contrast, young cells were hardly affected by the same PCDHA shRNA. Therefore, it was confirmed that cell adhesion by protocadherin is specific to senescent cells.

Figure 4B:
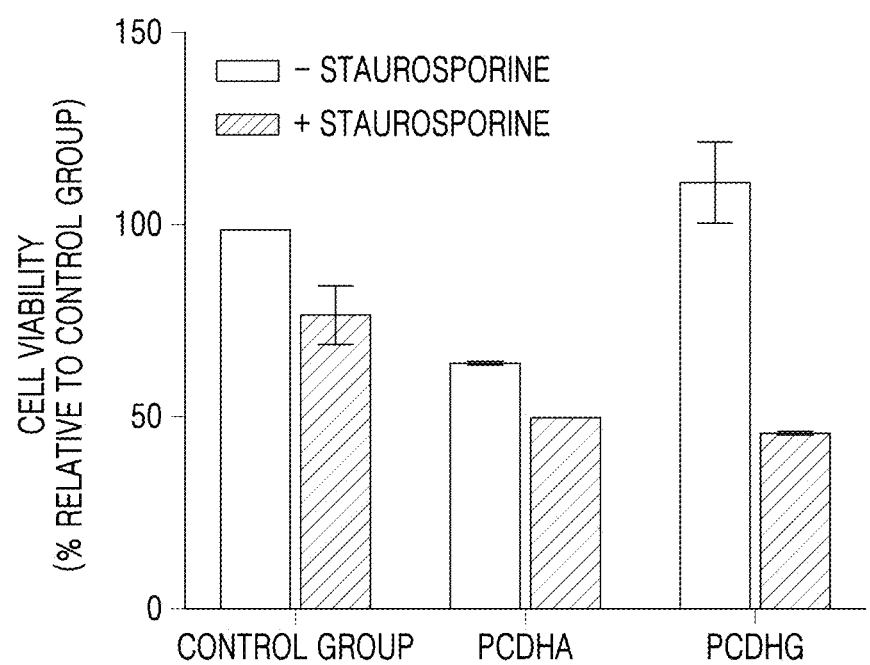
FIG. 4B is a graph showing cell viability (%) by counting the cells cultured in the presence of staurosporine.

Further, senescent cells are known to be resistant against drugs inducing cell apoptosis. After applying PCDHG shRNA to cells, 50 nM of staurosporine (Sigma, S4400) as an inducer of apoptosis was applied to the cells, and cultured under conditions of 37° C. and 5% $CO_2$ for about 24 hours. Thereafter, the number of the cultured cells was counted, and cell viability (%) was calculated. The result is shown in FIG. 4B. As shown in FIG. 4B, senescent cells resistant to cell apoptosis died.

Therefore, it was confirmed that protocadherin plays a role in maintenance and survival of senescent cells.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of separating senescent cells from a sample, the method comprising culturing a sample containing senescent cells and young cells in a culture dish without pretreatment of the culture dish for cell culture, wherein the senescent cells adhere to the culture dish, but the young cells do not adhere to the culture dish; removing the non-adherent young cells from the sample; and separating the adherent senescent cells from the culture dish.

2. The method of claim 1, wherein the senescent cells show an increased expression level of messenger RNA (mRNA) of protocadherin or a protocadherin protein than a young cell, an increased DNA methylation level in a protocadherin gene cluster than a young cell, β-galactosidase activity, a flat morphology, or a combination thereof.

3. The method of claim 1, wherein the culture dish does not comprise a coating with gelatin, collagen, fibronectin, polylysine, vitronectin, osteopontin, hydrogel, laminin, a fragment thereof, or a mimetic thereof does not comprise modification of the surface of the culture dish with a compound having a hydroxy group or a carboxyl group; does not comprise a coating with Matrigel; does not comprise a coating with an extracellular matrix or a fragment thereof; or a combination thereof.

4. The method of claim 1, wherein the culture dish is made of plastic, glass, or a combination thereof.

5. The method of claim 4, wherein the plastic is polystyrene.

6. The method of claim 1, wherein the culturing is performed for about 30 minutes to about 24 hours.

7. The method of claim 1, wherein separating the adherent senescent cells from the culture dish comprises applying trypsin, collagenase, hyaluronidase, DNase, elastase, papain, protease type XIV, or a combination thereof to the senescent cells adhering to the culture dish.

8. The method of claim 1, further comprising culturing the separated senescent cells in a cell culture vessel.

* * * * *